(12) United States Patent
Benum et al.

(10) Patent No.: US 10,941,350 B2
(45) Date of Patent: *Mar. 9, 2021

(54) USE OF SEMIPERMEABLE MEMBRANES IN CRACKING COILS

(71) Applicant: NOVA Chemicals (International) S.A., Fribourg (CH)

(72) Inventors: Leslie Wilfred Benum, Red Deer (CA); Michael Edward Koselek, Red Deer (CA); Vasily Simanzhenkov, Calgary (CA); Hany Iskandar Farag, Calgary (CA); Evan Geevouy Mah, Calgary (CA)

(73) Assignee: NOVA Chemicals (International) S A., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/340,403

(22) PCT Filed: Oct. 19, 2017

(86) PCT No.: PCT/IB2017/056510
§ 371 (c)(1),
(2) Date: Apr. 9, 2019

(87) PCT Pub. No.: WO2018/078494
PCT Pub. Date: May 3, 2018

(65) Prior Publication Data
US 2019/0241815 A1  Aug. 8, 2019

(30) Foreign Application Priority Data
Oct. 25, 2016  (CA) .................................. CA 2946264

(51) Int. Cl.
| | | |
|---|---|---|
| C10G 9/20 | (2006.01) | |
| B01J 19/00 | (2006.01) | |
| B01D 53/22 | (2006.01) | |
| B01D 71/02 | (2006.01) | |
| C01B 3/50 | (2006.01) | |
| C07C 7/144 | (2006.01) | |
| C10G 9/36 | (2006.01) | |
| F16L 9/02 | (2006.01) | |
| B01J 6/00 | (2006.01) | |
| B01D 69/02 | (2006.01) | |
| B01D 69/04 | (2006.01) | |
| B01D 69/10 | (2006.01) | |
| B01D 67/00 | (2006.01) | |
| C01B 3/34 | (2006.01) | |
| C07C 4/04 | (2006.01) | |
| C10G 25/00 | (2006.01) | |

(52) U.S. Cl.
CPC ........... *C10G 9/203* (2013.01); *B01D 53/228* (2013.01); *B01D 67/0067* (2013.01); *B01D 69/02* (2013.01); *B01D 69/04* (2013.01); *B01D 69/10* (2013.01); *B01D 71/02* (2013.01); *B01D 71/021* (2013.01); *B01D 71/022* (2013.01); *B01D 71/024* (2013.01); *B01D 71/025* (2013.01); *B01D 71/027* (2013.01); *B01J 6/008* (2013.01); *B01J 19/0013* (2013.01); *C01B 3/34* (2013.01); *C01B 3/503* (2013.01); *C01B 3/505* (2013.01); *C07C 4/04* (2013.01); *C07C 7/144* (2013.01); *C10G 9/36* (2013.01); *C10G 25/003* (2013.01); *F16L 9/02* (2013.01); *B01D 53/22* (2013.01); *B01D 2257/108* (2013.01); *B01D 2257/502* (2013.01); *B01D 2257/504* (2013.01); *B01D 2257/7025* (2013.01); *B01D 2325/02* (2013.01); *B01D 2325/023* (2013.01); *B01D 2325/04* (2013.01); *B01J 2219/00083* (2013.01); *C01B 2203/0216* (2013.01); *C01B 2203/041* (2013.01); *C01B 2203/1247* (2013.01); *C10G 2300/1081* (2013.01); *C10G 2300/201* (2013.01); *C10G 2300/207* (2013.01)

(58) Field of Classification Search
CPC ........ C10G 9/203; B01J 19/1893; C07C 4/04; C07C 7/144; B01D 71/027; B01D 71/025; B01D 53/228; B01D 69/02; B01D 69/04; B01D 69/10; B01D 67/0067; B01D 71/024; B01D 71/022; B01D 2257/7025; B01D 2257/504; B01D 2257/108; B01D 2257/502; B01D 2325/02; B01D 2325/04; C01B 3/503; C01B 3/505
See application file for complete search history.

(56) References Cited

U.S. PATENT DOCUMENTS

| | | |
|---|---|---|
| 5,959,718 A | 9/1999 | Morton |
| 6,152,987 A | 11/2000 | Ma |
| 7,727,596 B2 | 6/2010 | Ma |
| 8,167,976 B2 | 5/2012 | Del Paggio |

(Continued)

OTHER PUBLICATIONS

Haynes International ("HASTELLOY C-22"; https://www.haynesintl.conn/docs/default-source/pdfs/new-alloy-brochures/corrosion-resistant-alloys/brochures/c-22-brochure.pdf?sfvrsn=8) (Year: 2017).*

(Continued)

*Primary Examiner* — Lessanework Seifu
(74) *Attorney, Agent, or Firm* — Thomas James Styslinger

(57) ABSTRACT

A pass or tube or a section thereof or "U" bend in a coil in a paraffin cracker having section having a pore size in the metal substrate from about 0.001 to 0.5 microns over coated with a dense metal membrane permits the permeation of one or more of $H_2$, $CH_4$, CO and $CO_2$ from cracked gases moving the reaction equilibrium to the production of ethylene and reduces the load on the down-stream separation train of the steam cracker.

15 Claims, No Drawings

(56) References Cited

U.S. PATENT DOCUMENTS

| | | |
|---|---|---|
| 8,791,037 B1 | 7/2014 | Berchtold |
| 2004/0237780 A1* | 12/2004 | Ma .................. B01D 53/22 95/55 |
| 2015/0044130 A1 | 2/2015 | Tang |

OTHER PUBLICATIONS

Luo, Yi; Agren, Hans and Stafstrom, Sven; One- and Two-Photon Absorption Spectra of Short Conjugated Polyenes; Copyright 1994 American Chemical Society; J. Phys. Chem. 1994, 98, pp. 7782-7789.

Luo, Yi; Norman, Patrick; Macak, Peter and Agren, Hans; Solvent-Induced Two-Photon Absorption of a Push-Pull Molecule; J. Copyright 2000 American Chemical Society, Published on Web Mar. 24, 2000; Phys. Chem. A 2000, 104. pp. 4718-4722.

Macak, Peter; Luo, Yi; Norman, Patrick and Agren, Hans; Electronic and vibronic contributions to two-photon absorption of molecules with multi-branched structures; J. Chem. Phys. 113, 7055 (2000); https://doi.org/10.1063/1.1313559. Submitted: May 25, 2000. Accepted: Aug. 9, 2000. Published online: Oct. 19, 2000. pp. 7054-7061.

* cited by examiner

USE OF SEMIPERMEABLE MEMBRANES IN CRACKING COILS

TECHNICAL FIELD

The present invention relates to the field of thermally cracking paraffins. More particularly the present invention relates to incorporating permeable membranes for at least hydrogen in one or more of the coil passes or portions thereof or "U" bends to remove at least hydrogen from the cracked gasses upstream from the transfer line to reduce the load on the separation train.

BACKGROUND ART

In the back end of an ethylene steam cracker a significant amount of capital equipment and energy is used to separate the components of a cracked gas to obtain relatively pure ethylene, from methane and other components including $H_2$, CO, and $CO_2$. If some or all the $H_2$, $CH_4$, CO, and $CO_2$ could be separated from the cracked gases in the cracker it would drive the chemical equilibrium toward the formation of ethylene. Additionally such a separation would reduce the load on the separation train.

U.S. Pat. No. 6,152,987 issued Nov. 28, 2000 to Ma et al., from an application having an earliest filing date of Dec. 15, 1997 assigned to the Worcester Polytechnic Institute, Worcester Mass. teaches a micro porous stainless steel pipe having a surface coating of a hydrogen permeable membrane. The resulting tube or pipe may be used to separate hydrogen from a mixture of gasses. The reference does not suggest incorporating such a pipe structure in the pass of a furnace for thermally cracking paraffins to olefins.

The series of patents in the name of Ma et al., assigned to the Worcester Polytechnic Institute, is also illustrated by U.S. Pat. No. 7,727,596 issued Jun. 1, 2010 that teach separating hydrogen from a gaseous mixture at temperatures up to about 500° C. This is below the typical temperature for cracking paraffins. The gas mixture appears to be predominantly $H_2$ and helium rather than a cracked gas stream. There is no discussion of separating one or more of hydrogen, $CH_4$, CO, $CO_2$ from olefins (ethylene). Interestingly the patent discloses high temperature alloys having a pore size form 0.1 microns to 15 microns in some instances form 0.1 to 0.5 microns, which may be used as substrates for the separation membrane (Col. 7 lines 16-60).

United States Patent application 20150044130 published Feb. 12, 2015 in the name of Tang et al., assigned to Bettergy teaches doping zeolites with palladium to prepare a semipermeable membrane useful at temperatures up to about 450° C., again below cracking temperatures for paraffins (see the tables in the examples). The tables in the examples show a high selectivity for hydrogen over molecules such as $CO_2$, and $CH_4$ at temperatures up to about 450° C. The specification does not teach or suggest the membranes would be useful at temperatures above 450° C.

U.S. Pat. No. 8,791,037 issued Jul. 29, 2014 to Berchtold et al., assigned to the U.S. Department of Energy discloses a non oxide (Si/C/N) ceramic membrane from a polymeric precursor stable at temperatures up to about 1000° C. The specification teaches the pore size may be controlled by monomer composition, comonomer functionality, photopolymerization conditions and pyrolysis conditions (Col. 6 lines 40-50). However, no details of the conditions are disclosed in the patent.

The present invention seeks to provide a method to separate one or more of $H_2$, $CH_4$, CO, and $CO_2$ from a stream of cracked gases in a furnace coil.

DISCLOSURE OF INVENTION

In one embodiment the present invention provides a furnace coil for a [steam] cracker comprising one or more sections consisting of:
  i) a continuous metal passageway permitting the flow of cracked gasses there through having a melting temperature greater than 1000° C. adapted to co-operate with passes in the coil;
said metal having one or more areas comprising:
  a) a porosity so that from 5 to 75%, preferably 10 to 50%, of the pores having a size from 0.001 to 0.5 microns; or
  b) ceramic inserts in or over coating on said metal having a melting point greater than 900° C. and a porosity so that from 5 to 75%, preferably from 10 to 50%, of pores having a size from 0.001 microns to 0.5 microns;
said areas being over coated with a dense gas-selective membrane having a thickness from 0.1 to 10 microns permitting the diffusion of at least one of $H_2$, $CH_4$, CO and $CO_2$ at temperatures from 500° C. to 900° C. out of said passageway.

In a further embodiment the ceramic is formed from oxides, dioxides, nitrides, carbides and phosphates selected from the group consisting of porous silicon dioxide, fused silicon dioxide, porous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof.

In a further embodiment the dense gas-selective membrane comprises one or more of iron, nickel, titanium, chromium, aluminum, and molybdenum.

In a further embodiment the dense gas-selective membrane further comprises one or more metals selected from the group consisting of Pd, Ta, V, Pt, Nb and Zr.

In a further embodiment the dense gas-selective membrane further comprises one or more metal oxide ceramic selected from the group consisting of $Al_2O_3$, $BaTiO_3$, $SrTiO_3$ and $ZrO_2$.

In a further embodiment the dense gas-selective membrane is a dense metal oxide membrane.

In a further embodiment the dense gas-selective membrane comprises Pd.

In a further embodiment the dense gas-selective membrane comprises yttria stabilized $ZrO_2$.

In a further embodiment the dense gas-selective membrane comprises calcia stabilized $ZrO_2$.

In a further embodiment the dense gas-selective membrane is not less than about 95% of theoretical density.

In a further embodiment the ceramic is a Si/C/N ceramic formed by:
combining a monomeric and/or oligomeric silazane ceramic precursor with a comonomer comprising one or more of the group consisting of ene (vinyl) functionalized, oligomeric, inorganic or organic silazanes, difunctional thiols, and tetrafunctional thiols;
forming the combination as a thin film on a substrate;
photopolymerizing the thin film; and
pyrolyzing the photopolymerized thin film so as to result in a ceramic membrane that contains substantially no oxide.

In a further embodiment said monomeric and/or oligomeric silazanes contain heteroatoms selected from the group consisting of boron, titanium, aluminum, phosphorus, and combinations thereof.

In a further embodiment the continuous metal passage way is a tubular passage way forming part of the coil.

In a further embodiment the continuous metal passage way is a 90° bend (elbow) or a 180° bend (U bend) forming part of the coil.

A further embodiment provides a method to remove one or more of $H_2$, $CH_4$, CO, and $CO_2$ from cracked gasses in a furnace coil by incorporating one or more sections as above.

A further embodiment provides a cracking furnace comprising one or more coils as above.

A further embodiment provides a method for cracking a paraffin by passing it through a furnace coil according to claim 1, at a temperature from 850° C. to 950° C.

A further embodiment provides the method as above, wherein said paraffin is a $C_{2-4}$ paraffin.

A further embodiment provides the method as above wherein the paraffin is ethane.

DESCRIPTION OF EMBODIMENTS

Numbers Ranges

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

In steam cracking of paraffins such as naphtha and lower alkanes such as 02-4 paraffins, the feed together with steam is fed into tubes or coils passing through a convection section of the cracker where the feed is heated to close to cracking temperatures (about 750° C.). The feed then passes through coils in the radiant section of the furnace in a time from about 0.001 to 2.0 seconds in some embodiments from 0.001 to 1 second. In the radiant section of the furnace the coils comprise a number of straight sections or passes joined by elbows (90°) or "U" bends (180°) to provide a serpentine configuration. In the radiant section of the furnace wall mounted burners and, or floor mounted burners heat the walls to a temperature where they radiate heat onto the coil surfaces. The temperature of the coil is in the range from about 800° C. to about 975° C. At these temperatures the molecules are cracked, for example ethane is decomposed into its atomic components and rearranges to form a number of products including ethylene, $H_2$, $CH_4$, CO and $CO_2$. This rearrangement is a chemical reaction and removal of one or more of $H_2$, $CH_4$, CO and $CO_2$ by products from the gas stream in the coil will shift the conversion to the desired product ethylene.

The composition of the gases leaving the furnace contain many species including free radicals and need to be quenched quickly to prevent further rearrangement of the molecules in the stream. The cracked gas stream passes through a transfer line to a heat exchanger where the gas is quickly quenched to a temperature to prevent any significant rearrangement of the molecules in the gas. The quenched gas then enters a separation train. In the separation train the gas is sequentially cooled to low temperatures to condense methane, ethane and propane, and raffinates and other co-products. The co-products may include acetylene and other heavier products such as benzene, toluene and xylene (BTX). The product stream from the cracker also contains hydrogen, methane, carbon monoxide and carbon dioxide. These components also are cooled and pass through parts of the separation train. This puts an extra load on the separation train. It is desirable to reduce the amount of $H_2$, $CH_4$, CO and $CO_2$ in the cracked gasses prior to entering the separation train, preferably prior to entering the transfer line.

In accordance with the present invention there is provided a furnace coil for a steam cracker comprising one or more sections comprising a passageway, either sections of a pass, an elbow, or a "U" bend, of a metal.

The passage way (e.g. pass, pipe, tube elbow or "U" bend) line is typically cast from a metal having a melting point greater than 1000° C., desirably greater than 1100° C. The pass, elbow or "U" bend may be made of any high temperature steel. In some embodiments the pass or "U" bend is a stainless steel which may be selected from the group consisting of wrought stainless, austentic stainless steel and HP, HT, HU, HW and HX stainless steel, heat resistant steel, and nickel based alloys. The pass, elbow or "U" bend may be a high strength low alloy steel (HSLA); high strength structural steel or ultra high strength steel. The classification and composition of such steels are known to those skilled in the art.

Further examples of suitable metal components include, but are not limited to, iron, nickel, titanium, chromium, aluminum, and alloys thereof, e.g. steel, stainless steel, HASTELLOY® alloys (e.g. HASTELLOY C-22) (trademark of Haynes International, Inc., Kokomo, Ind.) and INCONEL® alloys (e.g. INCONEL alloy 625) (INCONEL is a trademark of Huntington Alloys Corp., Huntington W. Va.). In one embodiment, the transfer line includes an alloy containing chromium and nickel (e.g. INCONEL alloy 625). In an additional embodiment, the alloy contains chromium, nickel and molybdenum such as, for example, HASTELLOY C-22 or INCONEL alloy 625.

In one embodiment the stainless steel, preferably heat resistant stainless steel typically comprises from 13 to 50, preferably 20 to 50, most preferably from 20 to 38 weight % of chromium. The stainless steel may further comprise from 20 to 50, preferably from 25 to 50 most preferably from 25 to 48, desirably from about 30 to 45 weight % of Ni. The balance of the stainless steel may be substantially iron.

In some embodiments of the invention the steel may further comprise a number of trace elements including at least 0.2 weight %, up to 3 weight % typically 1.0 weight %, up to 2.5 weight % preferably not more than 2 weight % of manganese; from 0.3 to 2, preferably 0.8 to 1.6 typically less than 1.9 weight % of Si; less than 3, typically less than 2 weight % of titanium, niobium (typically less than 2.0, preferably less than 1.5 weight % of niobium) and all other trace metals; and carbon in an amount of less than 2.0 weight %. The trace elements are present in amounts so that the composition of the steel totals 100 weight %.

In one embodiment the stainless steel, preferably heat resistant stainless steel typically comprises from 13 to 50, preferably 20 to 50, most preferably from 20 to 38 weight % of chromium. The stainless steel may further comprise from 20 to 50, preferably from 25 to 50 most preferably from 25 to 48, desirably from about 30 to 45 weight % of Ni. The balance of the stainless steel may be substantially iron.

The present invention may also be used with nickel and/or cobalt based extreme austenic high temperature alloys (HTAs). Typically the alloys comprise a major amount of nickel or cobalt. Typically the high temperature nickel based alloys comprise from about 50 to 70, preferably from about 55 to 65 weight % of Ni; from about 20 to 10 weight % of Cr; from about 20 to 10 weight % of Co; and from about 5 to 9 weight % of Fe and the balance one or more of the trace elements noted below to bring the composition up to 100 weight %. Typically the high temperature cobalt based alloys comprise from 40 to 65 weight % of Co; from 15 to 20 weight % of Cr; from 20 to 13 weight % of Ni; less than 4 weight % of Fe and the balance one or more trace elements as set out below and up to 20 weight % of W. The sum of the components adding up to 100 weight %.

In some embodiments of the invention the steel may further comprise a number of trace elements including at least 0.2 weight %, up to 3 weight % typically 1.0 weight %, up to 2.5 weight % preferably not more than 2 weight % of manganese; from 0.3 to 2, preferably 0.8 to 1.6 typically less than 1.9 weight % of Si; less than 3, typically less than 2 weight % of titanium, niobium (typically less than 2.0, preferably less than 1.5 weight % of niobium) and all other trace metals; and carbon in an amount of less than 2.0 weight %. The trace elements are present in amounts so that the composition of the steel totals 100 weight %.

The substrate metal for the pass or part of a pass, elbow, or "U" bend may be porous. Porous stainless steel that is suitable for use as substrates are available from Mott Metallurgical Corporation (Farmington, Conn.) and from Pall Corporation (East Hills, N.Y.), for example.

One of ordinary skill in the art can select substrate thickness, porosity, and pore size distribution using techniques known in the art. Desired substrate thickness, porosity and pore size distribution can be selected based on, among other factors, the operating conditions of the final composite gas separation module such as operating pressure. Substrates having generally higher porosities and generally smaller pore sizes are particularly suited for producing composite gas separation modules. In some embodiments, the substrate can have a porosity in a range of about 5 to about 75% or about 10 to about 50%. While the pore size distribution of a substrate can vary, the substrate can have pore diameters that range from about 0.001 microns or less to about 0.1 microns or more typically from 0.001 to 0.05 microns, optionally from 0.001 to 0.01 microns.

Generally, smaller pore sizes are preferred. However, in some embodiments, a substrate having larger pores is used and an intermediate layer, typically a ceramic as disclosed below, having generally smaller pore sizes is formed on the porous substrate (e.g. a graded support is formed).

In some embodiments, the mean or median pore size of the substrate can range from about 0.001 to about 0.05 microns, e.g. from about 0.001 micron to about, 0.03, or 0.05, microns. In some instances, the pores in the substrate may be about 0.01 microns to an about 0.05 microns, e.g. 0.01 micron, 0.02 micron, and 0.05 micron size of pores may be present.

In some instances the pore size in the porous metal substrate may be large enough to permit molecules other than those desired (e.g. $H_2$, CO, $CO_2$ and $CH_4$) to pass through the metal. The porous metal substrate needs to be coated with a dense gas-selective membrane as described below. In a further embodiment the porous metallic substrate could be coated first with a ceramic and then with dense gas-selective membrane.

In some embodiments of the invention the metal substrate may be coated with a ceramic or have a ceramic insert (e.g. a pass through the metal is filled with a ceramic). The ceramic needs to be stable at temperatures not less than 450° C. preferably not less than 500° C., in some embodiments not less than 550° C. typically from 850° C. to 900° C. desirably up to 1000° C.

The ceramic should be porous ceramic formed from oxides, dioxides, nitrides, carbides and phosphates selected from the group consisting of porous silicon dioxide, fused silicon dioxide, porous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof. In some embodiments the ceramic membrane may be a dense gas-selective membrane as described below.

Preferred components for forming ceramic membranes include oxides of titanium, zirconium, aluminum (e.g. alpha alumina and gamma alumina), magnesium, silicon and mixtures thereof. Ceramics of mixed alumina and silicon oxide are zeolites and the titanium equivalents are ETS type ceramics. The pore size in the structure of the ceramic material may be from 0.0003 to 1.0 microns, in some embodiments from 0.001 to 1 micron or larger, in some embodiments from 0.01 to 0.05 microns. This pore size is sufficient to permit one or more of $H_2$, $CH_4$, CO and $CO_2$ to diffuse or permeate through the ceramic.

In some embodiments of the invention the ceramic may be doped with or contain, particles, fibers or whisker of a metal that helps transport one or more of hydrogen, methane, carbon monoxide and carbon dioxide. Palladium, niobium, tantalum, zirconium, vanadium and alloys thereof may be used for the transmission of hydrogen.

The ceramic may be applied in a dry or wet form. If in wet form (solution or suspension) typically the solvent/diluent is removed by a heat treatment to yield a dry coating. This step may take place at temperatures up to about 400° C. The dry coating is then sintered under an inert atmosphere typically nitrogen at temperatures up to about 1500° C. of a period of time from about 2 to 48 hours. The drying and sintering processes re well known to those skilled in the art.

In a further embodiment of the invention the gas selective (ceramic) membrane is formed from an inorganic polymeric precursor which is crosslinked by photo initiation and then pyrolised.

The materials further usefully employed in the polymeric ceramic aspect of the invention fall into two categories: the monomeric or oligomeric ceramic precursors and the multifunctional thiol monomers. The ceramic precursors of primary interest are vinyl functionalized, inorganic-organic silazanes. The composition and functionality of the thiolated comonomer is another variable that can be used to control the crosslinked polymer product properties. Non-oxygen containing alkane dithiols with varying chain lengths and tetrathiols both independently and in tandem are preferred.

Comonomer concentration (silazane/thiol), comonomer functionality (e.g. dithiol vs. tetrathiol and the ratio of the two when used in tandem), and dithiol chain length are system variables that allow for controlled manipulation of the polymerization kinetics, network formation characteristics, and correspondingly, the final properties of the polymer product.

Polymer films should be formed utilizing the photo-induced free-radical step-growth thiol-ene polymerization of the invention where the "ene" functionality is incorporated via the silazane ceramic precursor. Polymerization will preferably be conducted on bulk materials, i.e. no solvent is needed. The common UV photoinitiator, 2,2-dimethoxy-2-phenylacetophenone, will preferably be used to adjust the initiation kinetics. A unique feature of these thiol-ene reactions is their ability to self-initiate; therefore the use of a separate photoinitiator is optional, providing an additional level of control over the molecular composition and homogeneity of the polymer product.

The polymer material properties are intimately linked to the properties of the monomeric/oligomeric reactants, the polymerization mechanism utilized, the reaction conditions (temperature, atmosphere, initiation rate (irradiation intensity, initiator concentration, and self-initiating monomer concentration, and initiation wavelength(s))), and the extent of conversion of the reactive functionalities. All of these factors cumulatively dictate the polymerization kinetics and correspondingly, the material and chemical properties of the polymer product and thus, its separation characteristics.

Formation of an amorphous ceramic membrane is preferably accomplished by heating and pyrolysis of the polymeric ceramic precursor fabricated via the step-growth photopolymerization described previously. Just as the polymer fabrication conditions and kinetics play a large role in property determination, so do pyrolysis conditions and kinetics. Thus, an understanding of the dependence of the polymer/ceramic structure/properties on the material's thermal history is essential.

Pyrolysis of the crosslinked polymeric ceramic precursors should preferably be conducted in several different atmospheres, namely, under air, vacuum, nitrogen, argon, and ammonia, where the atmosphere dictates the pyrolysis chemistry and thus, relative Si—C—N compositions in the final product with attainable compositions ranging from pure SiC to pure $Si_3N_4$. The heating rate, ultimate temperature, soak time at temperature, and cooling rate are also preferably used to control the polymer to amorphous ceramic transition and thus, the product properties.

The polymerization reactions of the invention may be performed under varied conditions. For example, the reacting step optionally includes one or more of, e.g. irradiating a composition comprising the monomers, heating a composition comprising the monomers, adding at least one catalyst to a composition comprising the monomers, and/or the like. The radiation utilized may be, for example, electromagnetic radiation, electron bombardment, or nuclear radiation. In certain embodiments, for example, an article or other substrate coated with a polymerizable composition described herein is exposed to the radiation source (e.g. a UV or electron beam radiation source), for a selected period of time. To further illustrate, one photon and/or two photon polymerizations are optionally utilized. Additional details relating to single and multiple photon polymerizations are provided in, e.g. Macak et al. (2000) "Electronic and vibronic contributions to two-photon absorption of molecules with multi-branched structures", J. Chem. Phys. 113(17):7062; Luo et al. (2000) "Solvent induced two-photon absorption of push-pull molecules", J. Phys. Chem. 104:4718; and Luo et al. (1994) "One- and two-photon absorption spectra of short conjugated polyenes", J. Phys. Chem. 98:7782, which are each incorporated by reference. The intensity of light utilized to polymerize the monomers of the invention is typically between about 1 and about 1000 $mW/cm^2$, more typically between about 20 and about 800 $mW/cm^2$, and still more typically between about 50 and about 500 $mW/cm^2$, e.g. at wavelengths between about 315 and 365 nm. In addition, radiation exposure times are also varied, e.g. according to the particular monomer(s) used, the extent of double bond conversion desired, etc. To illustrate, the polymerizable compositions described herein are typically exposed to the particular radiation source from a few milliseconds to several minutes or more. In some embodiments, the monomers of the present invention achieve substantially complete or quantitative double bond conversion in less than 60 seconds (e.g. about 20 seconds or less) at 5 mW/cm, i.e., substantially quantitative double bond conversion is achieved at a dose typically less than 0.1 $J/cm^2$. Furthermore, polymerization temperatures are typically between 0° C. and 100° C. In preferred embodiments, polymerizations are performed at or near room temperature (e.g. 20-25° C.).

Following the polymerization reaction, the resultant polymeric material is typically pyrolyzed to form the ceramic material. For example, depending on the conditions employed for the thermal treatment, amorphous or crystalline structures can be obtained. Amorphous structures are generally obtained particularly when the pyrolysis is carried out in a temperature range from about 700 to 1200° C., preferably from 900 to 1200° C. When the thermal treatment is carried out at higher temperatures, for instance from 1200 to 2000° C., preferably from 1500 to 2000° C., at least partially crystalline structures are typically obtained. Pyrolysis is typically carried out under a protective gas cover or a reaction gas cover (e.g. helium, argon, nitrogen, ammonia, etc.) or in a vacuum. Further, pyrolysis is typically performed for about 0.5 to 2 hours to convert the polymeric material to a ceramic material. Optionally, a ceramic material is subjected to additional processing following pyrolysis. For example, a stable body is typically obtained after a sintering procedure at temperatures of up to 2000° C., preferably 1600-2000° C. for 0.5 to 2 hours.

The final ceramic coating or insert should have a porosity so that from 5 to 75%, preferably from 10 to 50%, of pores have a size from 0.001 microns to 0.05 microns.

The ceramic or metal substrate is then over coated with a dense gas selective membrane.

In one embodiment the gas selective membrane is a dense gas-selective membrane selectively permeable to hydrogen, and can include one or more hydrogen-selective metals or alloys thereof. ydrogen-selective metals include, but are not limited to, niobium (Nb), tantalum (Ta), vanadium (V), palladium (Pd), platinum (Pt), zirconium (Zr) and hydrogen-selective alloys thereof. Palladium and alloys of palladium are preferred. For example, palladium can be alloyed with at least one of the metals selected from the group consisting of gold, platinum, ruthenium, rhodium, yttrium, cerium and indium. Some care needs to be exercised in selecting components to use in the alloys. Copper and silver have been suggested as alloy components. However, as cracked gas may contain acetylene and steam one would avoid silver and copper as alloy components as there may be a tendency to form silver of copper acetylide which presents an explosive hazard. The metallic component may have a particle size from about 0.3 to about 3 microns.

The dense gas-separation membrane can include one or more components that are not gas-selective materials, e.g. components that are not hydrogen-selective materials such as metal oxide ceramics preferably selected from alumina ($Al_2O_3$), barium titanate ($BaTiO_3$), strontium titanate ($StTiO_3$), zirconia $ZrO_2$) stabilized or partially stabilized with yttria or calcia and various combinations thereof. When used the metal oxide ceramic may be present in an amount of from 10 to 90 wt. %, preferably from 30 to 70 wt. % desirably from 40 wt. % to 60 wt. % of the blend of the metal and metal oxide ceramic.

The dense gas-selective membrane may have a thickness from about 0.1 to 10 microns. For example, in one embodiment, the thickness of the dense gas-selective membrane is less than about 10 microns such as about 3 to 8 microns of substantially uniform thickness.

The metal components for the dense gas—selective membrane are generally activated by bringing them into contact with a solution of $SnCl_2$ (e.g. 1 g/l pH approximately 2) then filtering the powder from the solution shortly after contact and washing it and optionally drying it to obtain the activated metal ($PdCl_2$). The activated metal together with the metal oxide ceramic, if present, may be used as a powder or dispersed (slurry) or re-dissolved in a suitable solvent or diluent (e.g. water).

A layer of particulate material to form the dense gas phase selective membrane is brought into contact with the upper or outer surface of the porous ceramic or metal inserts (relative to the flow path of the cracked gas) by any suitable method known to those skilled in the art for applying a particulate material (e.g. powder) to a porous surface. For example, the particulate material may be applied to the surface of the porous metallic substrate or the ceramic by transport with a gas, or by application of a paste, a slurry or suspension of the particulate material, or by pressing or rubbing a powder of the particulate materials upon the surface of the porous insert.

In one embodiment at least one of the contacting steps is conducted while applying a pressure differential of a higher pressure and a lower pressure across the substrate (e.g. the porous metal substrate optionally coated with the ceramic) with the higher pressure being applied to the side of the upper or outer surface of the substrate. The application of the pressure differential can be accomplished through use of a negative pressure (i.e. vacuum applied to the other (e.g. lower or inner) surface of the substrate, or a positive pressure (i.e. pressure applied to the outer surface of the substrate), or a combination of the two. In preferred embodiments the particulate material is deposited as a slurry under the application of a vacuum to the second (i.e. inner) surface of the porous substrate.

The quantity and size of particulate material applied to the upper or outer surface of the porous insert (relative to the flow path of the cracked gas) can vary somewhat depending on the method utilized to deposit the particulate material. The primary goal in the application of particulate material is to completely cover the surface of the porous substrate that will ultimately support the dense gas selective (separation) membrane.

After the particulate material is placed in contact with the upper or outer surface of the porous substrate to form a first coated surface any excess first particulate material that is present on the insert is removed. The method of removal may vary depending upon the method of application but in most instances it may be removed by friction (e.g. mechanical or hand rubbing). Preferably, the step of removing the excess particulate material is conducted while a vacuum is applied to the lower or inner surface of the substrate (the surface opposite the applied particulate material). If the particulate material was deposited using a wet process (e.g. slurry or suspension) the coated substrate should be dried prior to removing the excess particulate material to avoid removing slabs of wet particulate cake which may pull particulate material from the pores of the porous substrate.

In some embodiments the application of the particulate material (metallic) components of a smaller particles size having an average particle diameter ranging, e.g. from about 0.001 to about 0.05 micron may be used to reduce the mean pore size of resulting coated porous substrate (support) and to reduce the surface roughness of the porous substrate. Achieving these goals involves addressing several variables in the selection of the particulate material (e.g. choice of particulate material, method of application, particle size, etc.).

The deposition of the dense phase gas-selective membrane may be carried out in one step or in multiple steps preferably with annealing after each step.

One useful method for annealing involves heat treating the coated porous substrate in an inert atmosphere at lower temperatures and thereafter in the presence of hydrogen. More specifically, the annealing takes place in the absence of hydrogen until the annealing temperature is at least 250° C., preferably at least 300° C. and more preferably at least 350° C. Once the annealing temperature reaches 250° C., preferably 300° C., and more preferably 350° C., hydrogen and oxygen can be present in the annealing step. Stated alternatively, in preferred embodiments the annealing step is conducted in a hydrogen containing atmosphere but only after the temperature has reached a minimum of 300° C., preferably at least 350° C. and more preferably at least 400° C. Although the annealing step can be taken to very high temperatures (e.g. 600° C. or greater), in most instances the annealing step occurs at temperatures between 350° C. and 550° C., and most preferably between 400° C. and 500° C. In embodiments where the membrane is built up by successive coatings, hydrogen is purged from the system as the membrane cools between deposition steps. Typically, hydrogen is purged by flooding the system with an inert gas as the membrane starts to cool so that no hydrogen is present as the membrane reaches 300° C., preferably 400° C.

Inert gases that may be used in this heat treatment step include nitrogen, helium, argon, neon and carbon dioxide. The preferred inert gas for use in the annealing step is one selected from the group consisting of nitrogen, argon, neon and carbon dioxide, and, the most preferred inert gas for use in the heat treatment is nitrogen.

The gaseous atmosphere under which the annealing step is conducted should have some hydrogen in it once the annealing temperature reaches at least 300° C. (preferably higher). The gaseous atmosphere used during the annealing step of the plated porous substrate should comprise a mixture of hydrogen from 3 to 100% and inert gas from 97 to 0%.

The annealing is conducted at a temperature that sufficiently treats the thin layer of gas-selective material (metal) that overlies the outer surface of the porous substrate (either the metal or metal coated with ceramic). While the required annealing temperature depends somewhat upon the particular metal or metal alloy that is plated upon the porous substrate and the thickness of the layer thereof, generally, the heat treatment temperature should be in the range of from at least 300° C. to 800° C. The preferred heat treatment temperature is in the range of from 325° C. to 700° C., and, most preferred, the heat treatment temperature is in the range of from 350° C. to 550° C.

The annealing step is conducted for a period of time sufficient to provide the necessary treatment of the layer of gas-selective material and where required prepare it for the next series of plating, polishing and annealing. The annealing time period may, thus, be in the range upwardly to 48 or more hours, but, a typical annealing time period is in the range of from 0.1 hours to 12 hours. It is preferred, however, for the annealing time to be minimized to only such a time necessary to provide the treatment of the layer of gas-selective metal required to achieve the benefits of the invention. It is expected that such a time period is in the range of from 0.2 to 10 hours, or even in the range of from 0.3 hours to 4 hours.

The pressure under which the annealing is conducted can be in the range of from 0.5 atmospheres (absolute) to 20 atmospheres. More typically, the heat treatment pressure is in the range of from 0.8 atm to 10 atm.

It is believed that the grain growth parameters of the deposited metal increases membrane stability and helps it resist change at elevated temperatures. Encouraging grain growth by increasing the annealing temperature appears to have a beneficial effect, particularly when the layers of gas selective material are polished between deposition steps. The polishing step is discussed in more detail below. It is thought that there is some positive effect in polishing the grains to effectively smear them into the open pores and form a uniform metal layer. Gas separation systems formed in such a manner have been observed to resist cracking at high operational temperatures.

After annealing, the porous substrate with its annealed supported membrane layer is polished/abraded. The polishing improves the surface of the deposited layer for further deposition by minimizing surface abnormalities and deformities and by filling openings such as cracks, pinholes and other imperfections that may be present in the thin membrane layer. Exemplary abrading and polishing methods are disclosed in U.S. Pat. No. 8,167,976 issued May 1, 2012 in the name of Del Paggio et al., assigned to Shell Oil Company.

In preparing the passes, elbows or "U" bends of the present invention one needs to try to match as far as practical the coefficients of thermal expansion of the various components to minimize internal stress between the different lays of the part and to minimize internal stress within a coating.

The tubes or "U" bends in accordance with the present invention may have a smooth interior or may have a spiral ridge inside to promote turbulent flow. Such an internal spiral ridge is disclosed in U.S. Pat. No. 5,959,718 issued Sep. 14, 1999 to Sugitani et al., assigned to Kubota Corporation. Without being bound by theory it is believed that turbulent flow at the inner surface of the passage way will promote diffusion of the lighter gasses in the cracked gas mixture. Separation in the "U" bends may be more efficient (per unit of length) as the gas travels around the "U" bend it is subjected to a centrifugal force.

The wall thickness of the "U" bends may not be uniform to account for erosion of the interior wall.

The passages of the present invention may optionally have a metal sheath about them. The sheath should be made of a metal having a melting temperature not less than about 1000° C., desirably greater than 1100° C. as described above relative to the metal from which the tube or "U" bend may be made from.

The passes or pipes should be relatively short section having a length not more than about 4 meters. If the pass sections have a sheath they should be positioned so that they are in a region of the furnace in which the pass is exposed to a relatively lower amount of radiant energy. This is to minimize the loss of surface energy in the entire pass (tubes and "U" bends). The gasses separated from the cracking pass will be accumulated to between the sheath and the external surface of the pipe or "U" tube. The sheath may have opening to permit the gas to exit into to the furnace where it will be burned. In some embodiments the openings in the sheath are designed so that the passage of combustion gasses past the openings draws gas between the sheath and the pass or "U" bend into the furnace (e.g. a venturi type tube). The temperatures in the radiant section of the furnace are sufficiently high that the gasses from the coil will be burned.

Some consideration needs to be given to the increase in temperature of the coil arising from the combustion of hydrogen at the coil surface. This may increase the temperature within the coil which might lead to carbon deposits inside the coil. Such deposits could block the pores. Some consideration also needs to be given to the effect of the resulting water on the radiant section of the furnace and particularly the passes or tubes. The combustion product should be water vapor but it may have an adverse effect on the radiant energy directed to the coil.

In some embodiments the sheath may direct the hydrogen to a collection means outside of the furnace.

In some embodiments the substrate metal may be machined to produce open sections which are be covered with or have inserts comprising one or more of the ceramic or the dense gas-selective membrane of the present invention.

The sheath serves an additional safety purpose in that if the substrate metal of the passageway should fail the sheath will provide some residual structural integrity to the pass permitting the plant to deal with the situation.

INDUSTRIAL APPLICABILITY

Creating an area in a furnace coil having a) a porosity so that from 5 to 75%, preferably 10 to 50%, of the pores having a size from 0.001 to 0.5 microns; or b) ceramic inserts in or over coating on said metal having a melting point greater than 900° C. and a porosity so that from 5 to 75%, preferably from 10 to 50%, of pores having a size from 0.001 microns to 0.5 microns; over coated with a dense gas-selective membrane having a thickness from 0.1 to 10 microns permitting the diffusion of at least one of $H_2$, $CH_4$, CO and $CO_2$ at temperatures from 500° C. to 900° C. out of said furnace coil shifts the chemical equilibrium in the coil to increase the production of ethylene.

The invention claimed is:

1. A furnace coil for a steam cracker comprising one or more sections consisting of:
   i) a continuous metal passageway permitting the flow of cracked gasses there through having a melting temperature greater than 1000° C. adapted to co-operate with passes in the coil;
   said metal having one or more areas comprising:
   a) a porosity so that from 5 to 75% of the pores having a size from 0.001 to 0.05 microns; or
   b) a ceramic over coating on said metal having a melting point greater than 900° C. and a porosity so that from 5 to 75% of pores having a size from 0.001 microns to 0.5 microns;
   said areas being over coated with a dense gas-selective membrane having a thickness from 0.1 to 10 microns permitting the diffusion of at least one of $H_2$, $CH_4$, CO and $CO_2$ at temperatures from 500° C. to 900° C. out of said passageway.

2. The furnace coil according to claim 1, wherein the metal or ceramic overcoating have a porosity so that from 10 to 50% of the pores have a size from 0.001 to 0.05 microns.

3. The furnace coil according to claim 2, wherein the ceramic is formed from oxides, oxides, nitrides, carbides and phosphates selected from the group consisting porous silicon dioxide, fused silicon dioxide, porous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof.

4. The furnace coil according to claim 3, wherein in said one or more sections the dense gas-selective membrane comprises one or more of iron, nickel, titanium, chromium, aluminum, and molybdenum.

5. The furnace coil according to claim 4, wherein the dense gas-selective membrane further comprises one or more metals selected from the group consisting of Pd, Ta, V, Pt, Nb and Zr.

6. The furnace coil according to claim 5, wherein the dense gas-selective membrane further comprises one or more metal oxide ceramic selected from the group consisting of $Al_2O_3$, $BaTiO_3$, $SrTiO_3$ and $ZrO_2$.

7. The furnace coil according to claim 6, wherein the dense gas-selective membrane is a dense metal oxide membrane.

8. The furnace coil according to claim 7, wherein in the dense gas-selective membrane comprises Pd.

9. The furnace coil according to claim 7, wherein the dense gas-selective membrane comprises yttria stabilized $ZrO_2$.

10. The furnace coil according to claim 7, wherein the dense gas-selective membrane comprises calcia stabilized $ZrO_2$.

11. The furnace coil according to claim 7, wherein the dense gas-selective membrane is not less than about 95% of theoretical density.

12. The furnace coil according to claim 2, wherein the ceramic is a Si/C/N ceramic formed by:
   combining a monomeric and/or oligomeric silazane ceramic precursor with a comonomer comprising one or more of the group consisting of ene (vinyl) functionalized, oligomeric, inorganic or organic silazanes, difunctional thiols, and tetrafunctional thiols;
   forming the combination as a thin film on a substrate;
   photopolymerizing the thin film; and
   pyrolyzing the photopolymerized thin film so as to result in a ceramic membrane that contains substantially no oxide.

13. The furnace coil according to claim 12, wherein said monomeric and/or oligomeric silazanes contain heteroatoms selected from the group consisting of boron, titanium, aluminum, phosphorus, and combinations thereof.

14. The furnace coil according to claim 1, wherein the continuous metal passage way is a tubular passage way forming part of the coil.

15. The furnace coil according to claim 1, wherein the continuous metal passage way is a 90° bend or a 180° bend forming part of the coil.

* * * * *